US006127602A

United States Patent [19]

Nichols

[11] Patent Number: 6,127,602

[45] Date of Patent: Oct. 3, 2000

[54] **PLANT CELLS AND PLANTS TRANSFORMED WITH *STREPTOCOCCUS MUTANS* GENES ENCODING WILD-TYPE OR MUTANT GLUCOSYLTRANSFERASE D ENZYMES**

[75] Inventor: Scott E. Nichols, Johnston, Iowa

[73] Assignee: Pioneer Hi-Bred International, Inc., Des Moines, Iowa

[21] Appl. No.: 09/008,172

[22] Filed: Jan. 16, 1998

Related U.S. Application Data

[62] Division of application No. 08/482,711, Jun. 7, 1995, abandoned.

[51] Int. Cl.$^7$ .......................... C12N 15/31; C12N 15/54; C12N 15/82; C12P 19/04; A01H 5/10

[52] U.S. Cl. .......................... 800/284; 800/276; 800/287; 800/288; 800/292; 800/293; 800/294; 800/317.2; 800/320; 800/320.1; 800/320.2; 800/320.3; 435/101; 435/193; 435/412; 435/417; 435/419; 435/440; 435/468; 435/469; 435/470

[58] Field of Search .................................... 800/284, 287, 800/276, 288, 298, 317.2, 320, 320.1, 320.2, 320.3, 292, 293, 294; 435/193, 101, 440, 468, 469, 470, 412, 417, 419

[56] References Cited

U.S. PATENT DOCUMENTS

| | | | |
|---|---|---|---|
| 4,202,966 | 5/1980 | Misaki et al. | 536/1.11 |
| 4,342,601 | 8/1982 | Yin | 536/123.12 |
| 4,597,830 | 7/1986 | April et al. | 536/123.12 |
| 4,734,162 | 3/1988 | Ampulski | 536/123.12 |
| 5,354,424 | 10/1994 | Rha et al. | 536/123.12 |
| 5,679,880 | 10/1997 | Curtiss, III et al. | 800/205 |
| 5,712,107 | 1/1998 | Nichols | 435/278.4 |
| 5,712,135 | 1/1998 | D'Halluin et al. | 435/172.3 |
| 5,985,666 | 11/1999 | Loiselle et al. | 435/419 |

FOREIGN PATENT DOCUMENTS

| | | | |
|---|---|---|---|
| 6 -313297 | 11/1994 | Japan . | |
| 6-287887 | 11/1994 | Japan . | |
| 1122354 | 8/1968 | United Kingdom . | |
| WO 95/13389 | 5/1995 | WIPO | C12N 15/82 |
| WO 96/01904 | 1/1996 | WIPO . | |
| WO96/06173 | 2/1996 | WIPO | C12N 15/54 |
| WO 97/29186 | 8/1997 | WIPO . | |
| WO 97/47808 | 12/1997 | WIPO . | |

OTHER PUBLICATIONS

Honda, O., et al. "Nucleotide sequence of the *Streptococcus mutans* gtfD gene encoding the glucosyltransferase–S enzyme" J. of General Microbiology (1990) 136, 2099–2105.

Napoli et al. "Introduction of a Chimeric Chalcone Synthase Gene into Petunia Results in Reversible Co–Suppression of Homologous Genes in trans" The Plant Cell (Apr. 1990) 2, 279–289.

von Schaewen, et al. "Expression of a yeast–derived invertase in the cell wall of tobacco and Arabidopsis plants leads to accumulation of carbohydrate and inhibition of photosynthesis and strongly influences growth and phenotype of transgenic tobacco plants " The EMBO Journal (1990) vol. 9 No. 10, pp. 3033–3044.

Kossman, et al. "Transgenic plants as a tool to understand starch biosynthesis" Carbohydrate Bioengineering (1995), Petersen et al.,eds., Elsevier Science, pp. 271–278.

Ueda et al. Sequence analysis of the gtfC gene from *Streptococcus mutans* GF–5, Gene. 69 (1988) pp. 101–109.

Gordon–Kamm, et al. "Transformation of Maize Cells and Regeneration of Fertile Transgenic Plants" *The Plant Cell*; vol. 2; pp. 603–618; (1990).

Gordon–Kamm, et al. "Transformation of Maize using Microprojectile Bombardment: An Update and Perspective" *In Vitro Cellular and Developmental Biology Plant 27P*; vol. 1; pp. 21–27; (1991).

Walbot & Messing "Gene Expression in Corn" *Corn and Corn Improvement*; Sprague and Dudley editors. 3$^{rd}$ edition (1988), pp. 418–421.

Schopke, et al. "Transformation in Cassava" *Biotechnology in Agriculture and Foresty*; vol. 23; pp. 273–289 (1993).

Lowe, et al. "Genetic Transformation in *Ipomoea batatas* (L.) Lam (Sweet Potato)" *Biotechnology in Agriculture and Forestry*, vol. 29; pp. 308–320 (1994).

Juboory, et al. "In Vitro Regeneration of Agrobacterium–Transformed Sweet Potato (*Ipomoea batatas* L.)" *PGRSA Quarterly*; vol. 19, No. 2, pp. 82–89 (1991).

Prakash, et al. "Genetic transformation of sweet potato by particle bombardment" *Plant Cell Reports*; vol. 11, pp. 53–57 (1992).

Fromm, et al. "Inheritance and Expression of Chimeric Genes in the Progeny of Transgenic Maize Plants " *Bio/Technology*; vol. 8; pp. 833–839 (1990).

Weising, et al. "Foreign Genes in Plants: Transfer, Structure, Expression, and Applications" *Annual Rev. Genetic*; vol. 22, pp. 421–477 (1988).

*Primary Examiner*—David T. Fox
*Attorney, Agent, or Firm*—Pioneer Hi-Bred International, Inc.

[57] ABSTRACT

The present invention provides methods of making paper utilizing glucans, produced by glucosyltransferase D enzymes of the species *Streptococcus mutans*, instead of modified starches. The present glucans are functionally similar to the hydroxethyl modified starch and are particularly useful in the sizing and coating steps of paper manufacture. The present glucans also exhibit thermoplastic properties and impart gloss to the paper during the coating step. In particular, the present invention provides plant cells and plants transformed with *Streptococcus mutans* genes encoding wild-type or mutant glucosyltransferase D enzymes.

9 Claims, No Drawings

PLANT CELLS AND PLANTS TRANSFORMED WITH *STREPTOCOCCUS MUTANS* GENES ENCODING WILD-TYPE OR MUTANT GLUCOSYLTRANSFERASE D ENZYMES

This application is a divisional of U.S. patent application Ser. No. 08/482,711, filed on Jun. 7, 1995, now abandoned.

FIELD OF THE INVENTION

The present invention involves the field of paper manufacture. Specifically, the present invention provides sources alternative to modified starch in paper manufacture.

BACKGROUND OF THE INVENTION

There are three major phases in paper manufacture where starch is used as an ingredient. The first is the "wet end" where cellulose fibers are mixed with starch in a slurry, and the slurry is forced through a narrow opening onto a wire belt. Water is rapidly removed as the forming sheet travels the length of the belt. After a distance of typically five to fifteen meters on the belt, the sheet has had enough water removed from it so that it can support its own weight. The sheet travels through a number of foils and rolls wherein more water is removed. It is dried to about 11% moisture.

The second phase in paper manufacturing involving starch is the "sizing step". Here, the paper goes through a sizing press where a starch slurry is applied to the sheet. The sheet again goes through a series of foils and rolls. It is dried on rollers and can be taken off the press as a finished product.

The third step involves coating the paper with a mixture of starch and a thermoplastic molecule. On certain lines, this occurs after the sizing step. The nascent roll can also be removed and reinstalled onto a different press for coating. A typical coating device has two blades that run the width of the paper. The blades apply the coating material onto two rolling drums. The paper passes between the drums and the coating material, comprising starch and the thermoplastic moiety, comes off the drums onto the paper. After the paper leaves the drums, it goes through a number of dryers. When the paper is dry, it goes onto a "soft calendar" comprising two drums, one made of a hard density fabric and the other a heated steel drum. The paper passes between the two drums and the heated steel drum is sufficiently hot to melt thermoplastic components of the coating mix providing a hard gloss finish on the paper.

The cellulosic wood pulp fibers, typically used in the above process, are anionic in nature. The addition of a cationic starch to the "wet end" slurry acts as an adhesive by cross linking the pulp fibers through salt linkages. Thus a cross linked polymeric network is made, comprising the starch and cellulose fibers. Typically, the cationic starches used in the "wet end" are tertiary or quaternary amines. These amino groups are added to the starch by wet millers.

Surface sizing starches are used to impart both strength and smooth finish to the sheet after it leaves the "wet end". Such starches also prepare the sheet to receive the various coatings. In cheaper grades of paper and in fiberboard manufacture, sizing starches are used simply as unmodified corn starch. For high grades of paper, chemically-modified starches are used. This is important for the application of a smooth, uniform high quality surface to the paper.

There is a tendency for starches to retrograde i.e. re-form high ordered structures (both helices and crystallites) in an otherwise gelatinous starch slurry. Deposition of retrograded starch onto high quality paper causes regional inconsistencies on the paper and is unacceptable. Furthermore, retrograded starch in the sizing press may necessitate shutting the line down to clear the apparatus.

The starch most often used for sizing applications is a starch having a covalently attached neutral adduct, for instance hydroxyethyl starch. This is prepared by the reaction of ethylene oxide with starch after it is isolated at the wet milling plant. The function of the hydroxyethyl (or similar) adduct is independent of its chemical nature; rather, it serves to provide steric hindrance, inhibiting the formation of high ordered structures. This steric hindrance is critical to decrease retrogradation. The periodic protuberance afforded by the adduct disrupts the formation of higher ordered structures that leads to retrogradation.

Speed is of paramount importance in paper manufacturing. Limiting in press speed is starch consistency. Presses often run below their full capacity speeds. Depending on the application, starch slurries are between 3–15% (usually 5–6%) solids. An increase in solids would necessarily result in a decrease in the amount of water that would have to be removed from a paper sheet being manufactured. This would allow the press to work at higher speeds.

Hydroxethylated starch also forms higher ordered structures as the temperature decreases or the concentration increases. The formation of the higher ordered structures on the surface of the paper is required. After application to the sheet the starch reforms some of these higher ordered structures and creates a uniform surface that imparts structural strength and facilitates the acceptance of inks and dyes. However, the higher ordered structures should not form in the slurry nor on the application device because this necessitates shutting down the production line to clear off retrograded starch.

The function of the hydroxyethyl group is to lower the temperature and/or raise the concentration of starch at which retrogradation occurs. As the processing lines have already been optimized for a particular temperature of the starch slurry, a decrease in the tendency to retrograde would allow for a higher carbohydrate content in the slurry.

The mixture applied to the paper sheet in the coating process contains hydroxethylated starch and thermoplastic molecules. The most prevalent thermoplastic molecules used are latexes, such as styrene butadiene. The function of the hydroxethyl starch is as indicated above. The function of the thermoplastic molecule is to form a high gloss finish on the paper. This causes an increased ability to take inks and dyes and improves the resolution, in general, on the printed sheet.

Based on the foregoing, there exists a need, in paper manufacturing, for modified starch substitutes which are functionally similar to modified starch. There is a further need to provide substitutes for modified starch which are less prone to retrogradation. There is a further need to provide methods of manufacturing paper which are faster than current methods and allow presses to run closer to their full capacity speed. There is a further need to provide methods of manufacturing paper that are environmentally-friendly and do not involve input materials that require chemical processing.

It is therefore an object of the present invention to provide substitutes for modified starch which are less prone to retrogradation when used in paper manufacture.

It is a further object of the present invention to provide methods of manufacturing paper which are faster and more efficient than existing methods.

It is a further object of the present invention to provide substitutes for starch in paper manufacturing that do not require costly chemical modification as does starch.

It is a further object of the present invention to provide methods for manufacturing paper that are more environmentally-friendly than existing methods.

It is a further object of the present invention to provide substitutes for thermoplastic molecules currently used in the coating step during paper manufacture.

SUMMARY OF THE INVENTION

The present invention provides glucans which can be used as substitutes for modified starch and/or latexes in paper manufacture. The present glucans are produced by glucosyltransferase D ("GTF D") enzymes of the species *Streptococcus mutans*, and are functionally similar to the modified starch currently used in paper manufacture. The present glucans also exhibit similar physical properties to thermoplastic molecules currently used in the coating step during paper manufacture.

The present invention also provides methods of making paper utilizing the present glucans, input materials that are produced biologically. Thus the present methods are more cost-effective and environmentally-friendly than current methods which require input materials that produce chemical effluents.

DETAILED DESCRIPTION OF THE INVENTION

Sequences

Seq. I.D. No. 1—the gtfd cDNA sequence

Seq. I.D. No. 2—the gtfd protein sequence encoded by Seq. I.D. No. 1

As used herein, "glucan" means a glucose polymer having linkages that are α(1→3), α(1→6) and branching α(1→3,6).

As used herein, "amyloplast" means starch accumulating organelle in plant storage tissue.

As used herein, "vacuole" means the cellular compartment bounded by the tonoplast membrane.

*Streptococcus mutans* is a species that is endogenous to the oral cavity and colonizes tooth enamel. See e.g. Kuramitsu, "Characterization of Extracellular Glucosyl Transferase Activity of *Strepotococcus mutans*," *Infect. Immun.*; Vol. 12(4); pp.738–749; (1975); and Yamashita, et al., "Role of the *Streptococcus mutans* gtf Genes in Caries Induction in the Specific-Pathogen-Free Rat Model," *Infect. Immun.*; Vol. 61(9); pp. 3811–3817; (1993); both incorporated herein their entirety by reference. *Streptococcus mutans* species secrete glucosyltransferase D ("GTF D") enzymes which utilize dietary sucrose to make a variety of extracellular dextrans. See e.g. Kametaka, et al., "Purification and Characterization of Glucosyltransferase from *Streptococcus mutans* OMZ176 with Chromatofocusing," *Microbios*; Vol. 51(206); pp. 29–36; (1978); and Honda, et al., "Nucleotide Sequence of the *Streptococcus mutans* gtf Gene Encoding the Glucosyltransferase-S Enzyme," *J. Gen. Microbiol.*; Vol. 136; pp. 2099–2105; (1990); both incorporated herein by reference.

Both soluble and insoluble glucans are synthesized, and the proteins responsible have been isolated and characterized. See e.g. Aoki, et al., "Cloning of a *Streptococcus mutans* Glucosyltransferase Gene Coding for Insoluble Glucan Synthesis," *Infect. Immun.*; Vol. 53(3); pp. 587–594; (1986); Shimamura, et al., "Identification of Amino Acid Residues in *Streptococcus mutans* Glucosyltransferases Influencing the Structure of the Glucan Produced," *J. Bacteriol.*; Vol. 176(16); pp. 4845–4850; (1994); and Kametaka, et al., "Purification and Characterization of Glucosyltransferase from *Streptococcus mutans* OMZ176 with Chromatofocusing," *Microbios*; Vol. 51(206); pp. 29–36; (1987); all incorporated herein their entirety by reference.

The proteins involved are large (~155 kDa) and catalyze the group transfer of the glucosyl portion of sucrose to an acceptor glucan via α(1→3) and α(1→6) linkages. See e.g. Wenham, et al., "Regulation of Glucosyl Transferase and Fructosyl Transferase Synthesis by Continuous Cultures of *Streptococcus mutans*," *J. Gen. Microbiol.*; Vol. 114(Part 1); pp. 117–124; (1979); Fu, et al., "Maltodextrin Acceptor Reactions of *Streptococcus mutans* 6715 glucosyltransferases," *Carbohydr. Res.*; Vol. 217; pp. 210–211; (1991); and Bhattacharjee, et al., "Formation of Alpha—(1→6), Alpha—(1→3), and Alpha (1→2) Glycosidic Linkages by Dextransucrase from *Streptococcus sanguis* in Acceptor-Dependent Reactions," *Carbohydr. Res.*, Vol. 242; pp. 191–201; (1993); all incorporated herein their entirety by reference.

The genes involved in glucan synthesis have been isolated and sequenced. See Shimamura, et al., cited above; Russel, et al., "Expression of a Gene for Glucan-binding Protein from *Streptococcus mutans* in *Escherichia coli*," *J. Gen. Microbiol.*; Vol. 131(2); pp.295–300; (1985); Russell, et al., "Characterization of Glucosyltransferase Expressed from a *Streptococcus sobrinus* Gene Cloned in *Escherichia coli*," *J. Gen. Microbiol.*, Vol. 133(4); pp. 935–944; (1987); and Shimamura, et al., "Identification of Amino Acid Residues in *Streptococcus mutans* Glucosyltransferases Influencing the Structure of the Glucan Product," *J. of Bacteriol.*; Vol. 176(16); pp. 4845–4850; (1994); and Shiroza, et al., "Sequence Analysis of the GTF D Gene from *Streptococcus mutans*," *J. Bacteriol.*; Vol. 169(9); pp. 4263–4270; (1987); all incorporated herein in their entirety by reference.

The structures of the various glucans produced by GTF D enzymes are quite heterogeneous with respect to the proportions of α(1→3), α(1→6) and α(1→3,6) branches present in any given glucan. Transformation of genes which encode naturally occurring GTF D and GTF D mutant proteins into plants, such as maize, provides amyloplasts and vacuoles with novel compositions.

GTF D enzyme activity incorporated into the amyloplast and/or vacuole leads to the accumulation of starch and glucan in the same amyloplast and/or vacuole. Retrogradation occurs as portions of starch molecules interact and subsequently form inter- or intra-chain helices. In a mixture of starch and glucans, the frequency of starch—starch interactions that lead to helix formation is diminished. A paste made from the mixed polymers is less prone to retrogradation as a result. This is especially true in the starch accumulation mutants envisioned as transformation targets where the relative proportion of starch is reduced.

Glucans produced in maize amyloplasts and/or vacuoles by the transgenic GTF D enzymes can function in paper processing without chemical modification, as required of starch. The polymer solution consequently has altered rheological properties and is less prone to retrogradation composed to starch. The glucans are branched and irregular and able to supplant modified starches with comparable or superior efficacy. They do not require any costly chemical modification as does starch. For coating applications, the present glucans exhibit thermoplastic properties in addition to the above advantages.

The wild type GTF and mutants thereof useful in producing glucans according to the present invention are provided below. The following code is employed:

| Amino Acid | One-letter Symbol |
|---|---|
| Alanine | A |
| Asparagine | N |
| Aspartic Acid | D |
| Glutamine | Q |
| Glutamic Acid | E |
| Isoleucine | I |
| Lysine | K |
| Threonine | T |
| Tyrosine | Y |
| Valine | V |

The nomenclature used to identify the mutant GTF D enzymes used to produce the present glucans is as follows: the number refers to the amino acid position in the polypeptide chain; the first letter refers to the amino acid in the wild type enzyme; the second letter refers to the amino acid in the mutated enzyme; and enzymes with multiple mutations have each mutation separated by /.

The mutant GTF D enzymes used to produce glucans for paper coating are preferably selected from the group consisting of the wild type of the enzyme; T589D; T589E; N471D; N471D/T589D; and N471D/T589E; more preferably from the group consisting of the wild type; N471D; N471D/T589D; and N471D/T589E; even more preferably from the group consisting of the wild type and N471D. The wild type of the enzyme is the most preferred.

The mutant GTF D enzymes used to produce glucans for paper sizing are preferably selected from the group consisting of the wild type of the enzyme; T589D; T589E; N471D; N471D/T589D; and N471D/T589E; more preferably from the group consisting of N471D; N471D/T589D; and N471D/T589E; most preferably N471D.

The glucans of the present invention are preferably produced in transgenic maize, potato, cassava, sweet potato, rye, barley, wheat, sorghum, oats, millet, triticale, sugarcane or rice. More preferably, the present glucans are produced in maize, potato, cassava, or sweet potato. Even more preferably, the present glucans are produced in maize or potato. Most preferably, the present glucans are produced in maize.

In a highly preferred embodiment of the present invention, maize lines deficient in starch biosynthesis are transformed with mutant GTF D genes. Such lines may be naturally occurring maize mutants (i.e. $sh_2$, $bt_2$, $bt_1$) or transgenic maize engineered so as to accumulate low amounts of starch in the endosperm when compared to wild type maize. See e.g. Müller-Röber, et al., "Inhibition of the ADP-glucose Pyrophosphorylase in Transgenic Potatoes Leads to Sugar-Storing Tubers and Influences Tuber Formation and Expression of Tuber Storage Protein Genes," *The EMBO Journal*; Vol. 11(4); pp. 1229–1238; (1992); and Creech, "Carbohydrate Synthesis in Maize," *Advances in Agronomy*; Vol. 20; pp. 275–322; (1968); both incorporated herein in their entirety by reference.

The production of the present glucans is performed according to methods of transformation that are well known in the art, and thus constitute no part of this invention. The compounds of the present invention are synthesized by insertion of an expression cassette containing a synthetic gene which, when transcribed and translated, yields a GTF D enzyme or mutant that produces the desired glucan. Such empty expression cassettes, providing appropriate regulatory sequences for plant expression of the desired sequence, are also well-known, and the nucleotide sequence for the synthetic gene, either RNA or DNA, can readily be derived from the amino acid sequence for the protein using standard texts and the references provided. The above-mentioned synthetic genes preferably employ plant-preferred codons to enhance expression of the desired protein.

The following description further exemplifies the compositions of this invention and the methods of making and using them. However, it will be understood that other methods, known by those of ordinary skill in the art to be equivalent, can also be employed.

The genes which code for the present mutants can be inserted into an appropriate expression cassette and introduced into cells of a plant species. Thus, an especially preferred embodiment of this method involves inserting into the genome of the plant a DNA sequence coding for a mutant or wild type in proper reading frame, together with transcription promoter and initiator sequences active in the plant. Transcription and translation of the DNA sequence under control of the regulatory sequences causes expression of the protein sequence at levels which provide an elevated amount of the protein in the tissues of the plant.

Synthetic DNA sequences can then be prepared which code for the appropriate sequence of amino acids of a GTF D protein, and this synthetic DNA sequence can be inserted into an appropriate plant expression cassette.

Likewise, numerous plant expression cassettes and vectors are well known in the art. By the term "expression cassette" is meant a complete set of control sequences including promoter, initiation, and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

By the term "vector" herein is meant a DNA sequence which is able to replicate and express a foreign gene in a host cell. Typically, the vector has one or more restriction endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant".

A particularly preferred vector is a plasmid, by which is meant a circular double-stranded DNA molecule which is not a part of the chromosomes of the cell.

As mentioned above, both genomic DNA and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

The expression cassette comprising the structural gene for a mutant of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. Typhimurium*, and *Serratia marcescens*. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of the GFT D protein.

It will also be appreciated by those of ordinary skill that the plant vectors provided herein can be incorporated into *Agrobacterium tumefaciens*, which can then be used to transfer the vector into susceptible plant cells, primarily from dicotyledonous species. Thus, this invention provides a method for introducing GTF D in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention.

For example, the potato plant can be transformed via *Agrobacterium tumefaciens* to produce the present glucans. The transformation cassette comprises a patatin promoter, followed by the relevant GTF D coding sequence and the neomycin phosphotransferase polyadenylation site/terminator. See e.g. Utsumi, et al., "Expression and Accumulation for Normal and Modified Soybean Glycinins in Potato Tubers," *Plant Science*; Vol. 102(2); pp. 181–188; (1994); (Limerick); incorporated herein in its entirety by reference. The transgenic cassette is placed into a transformation vector. For example, BIN19, or derivatives thereof, are useful when transforming via *Agrobacterium tumefaciens*. See e.g. Visser, et al., "Transformation of Homozygous Diploid Potato with an *Agrobacterium tumefaciens* Binary Vector System by Adventitious Shoot Regeneration on Leaf and Stem Segments," *Plant Mol. Biol.* Vol. 12(3); pp. 329–338; (1989); incorporated herein in its entirety by reference.

For maize transformation vectors, the promoters include any promoter whose expression is specific and limited to endosperm cells. Included are those encoding either 22 kDa zein, opaque2, gamma zein and waxy. These lead into the GTF D gene and are followed by the endogenous terminator or the heterogeneous PINII terminator.

The GTF D protein is directed to the maize endosperm amyloplast using a suitable transit sequence. Transit sequences useful in directing the enzyme into the amyloplast for accumulation within the amyloplast include but are not limited to ribulose biphosphate carboxylase small subunit, waxy, brittle-1, and chlorophyll AB binding protein. The transit sequences are juxtaposed between the promoter and the GTF D coding sequence and fused in translational reading frame with the GTF D moiety.

Transit sequences useful in directing the enzyme into the vacuole for accumulation within the vacuole are well known in the art. For vacuolar targeting, see e.g. Ebskamp, et al., "Accumulation of Fructose Polymers in Transgenic Tobacco," *Bio/Technology*; Vol. 12; pp. 272–275; (1994); incorporated herein in its entirety by reference.

For maize transformation and regeneration see e.g. Armstrong, C., (1994), "Regeneration of Plants from Somatic Cell Cultures: Applications for in vitro Genetic Manipulation," *The Maize Handbook*, Freeling, et al. eds, pp. 663–671; incorporated herein in its entirety by reference.

Once a given plant is transformed, the glucans synthesized can be isolated, by standard methods, known to one skilled in the art. The glucans thus obtained in the transgenic plant can be substituted for modified starches and utilized in the sizing and/or coating steps. For formulations useful in the coating step, see e.g. Heiser, et al., "Starch Formations," *Starch and Starch Products in Paper Coating*; Kearney, et al., eds., pp. 147–162; (1990); Tappi Press; incorporated herein in its entirety by reference.

In both sizing and coating, the present glucans are utilized in an amount of from about 4–15% w/v, more preferably from about 5–12% w/v, also preferably from about 6–8% w/v. Weight percent is defined as grams of molecule per 100 ml solution.

The present glucans are used to replace the starch and/or latex molecules completely, or a starch-glucan or a latex-glucan mixture is used in the slurry. In the sizing application, the glucan:starch ratio ranges from about 10:90 to about 100:0; more preferably from about 40:60 to about 100:0; more preferably still from about 60:40 to about 100:0; most preferably about 100:0.

In the coating application, the glucan:starch ratio ranges from about 10:90 to about 100:0; more preferably from about 40:60 to about 100:0; more preferably still from about 60:40 to about 100:0; most preferably about 100:0. The glucan:latex ratio ranges from about 10:90 to about 100:0; more preferably from about 40:60 to about 100:0; more preferably still from about 60:40 to about 100:0; most preferably about 100:0.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What claimed is:

1. A transgenic plant cell containing a DNA molecule encoding *Streptococcus mutans* glucosyltransferase D enzyme, wild type or mutant, wherein the mutant is T589D; T589E; N471D; N471D/T589D; or N471D/T589E, and wherein the plant cell is derived from a plant selected from the group consisting of potato, cassava and sweet potato.

2. The plant cell of claim 1 which is transformed by *Agrobacterium tumefaciens*, electroporation, retroviruses, bombardment or microinjection.

3. The plant cell of claim 1 wherein the enzyme produces a glucan in the amyloplast or vacuole of the plant cell.

4. A transgenic plant regenerated from the plant cell of claim 1.

5. A transgenic plant seed containing a DNA molecule encoding *Streptococcus mutans* glucosyltransferase D enzyme, wild type or mutant, wherein the mutant is T589D; T589E; N471D; N471D/T589D; or N471D/T589E and wherein the plant seed is derived from a plant selected from the group consisting of maize, rye, barley, wheat, sorghum, oats, millet, triticale and rice.

6. The maize seed of claim 5 wherein the seed is from a maize line deficient in starch biosynthesis.

7. The seed of claim 6 wherein the plant is maize of genotype $sh_2$, $bt_2$ or $bt_1$.

8. The seed of claim 6 wherein the enzyme produces an insoluble product.

9. The plant seed of claim 5 wherein the DNA molecule contains a promoter selected from the group consisting of 22 kDa zein, opaque2, gamma zein and waxy gene promoters.

* * * * *

SEQUENCE LISTING

```
<160> NUMBER OF SEQ ID NOS: 2

<210> SEQ ID NO 1
<211> LENGTH: 4310
<212> TYPE: DNA
<213> ORGANISM: Streptococcus mutans
<220> FEATURE:
<221> NAME/KEY: CDS
<222> LOCATION: (5)...(4295)

<400> SEQUENCE: 1

tttt atg gaa acc aaa cga cgt tac aaa atg cac aag gtt aaa aag cac      49
     Met Glu Thr Lys Arg Arg Tyr Lys Met His Lys Val Lys Lys His
      1               5                  10                  15

tgg gta acc gtt gct gtc gct tct ggt ttg att acc ttg ggg acc aca       97
Trp Val Thr Val Ala Val Ala Ser Gly Leu Ile Thr Leu Gly Thr Thr
                 20                  25                  30

aca ctg gga agc tca gtt tca gca gaa aca gaa cag cag acc tca gat      145
Thr Leu Gly Ser Ser Val Ser Ala Glu Thr Glu Gln Gln Thr Ser Asp
             35                  40                  45

aaa gtg gta act cag aaa agt gag gat gat aag gcg gca tct gaa tcc      193
Lys Val Val Thr Gln Lys Ser Glu Asp Asp Lys Ala Ala Ser Glu Ser
         50                  55                  60

agc caa aca gat gca cct aaa act aag caa gca caa aca gaa caa acg      241
Ser Gln Thr Asp Ala Pro Lys Thr Lys Gln Ala Gln Thr Glu Gln Thr
     65                  70                  75

cag gcc caa agt cag gca aac gtt gct gat aca agc act agc ata act      289
Gln Ala Gln Ser Gln Ala Asn Val Ala Asp Thr Ser Thr Ser Ile Thr
 80                  85                  90                  95

aag gaa act cct tca caa aat att aca aca caa gcc aac tct gat gac      337
Lys Glu Thr Pro Ser Gln Asn Ile Thr Thr Gln Ala Asn Ser Asp Asp
                100                 105                 110

aaa aca gta aca aat acg aaa tca gaa gaa gca caa act tct gaa gag      385
Lys Thr Val Thr Asn Thr Lys Ser Glu Glu Ala Gln Thr Ser Glu Glu
            115                 120                 125

cgc aca aag caa tca gaa gaa gca cag act act gct tcc agt cag gct      433
Arg Thr Lys Gln Ser Glu Glu Ala Gln Thr Thr Ala Ser Ser Gln Ala
        130                 135                 140

tta aca cag gca aaa gct gaa tta aca aag caa aga caa aca gca gct      481
Leu Thr Gln Ala Lys Ala Glu Leu Thr Lys Gln Arg Gln Thr Ala Ala
    145                 150                 155

caa gaa aat aaa aat cct gtt gac tta gcg gcc att cca aat gtg aaa      529
Gln Glu Asn Lys Asn Pro Val Asp Leu Ala Ala Ile Pro Asn Val Lys
160                 165                 170                 175

caa att gat ggc aaa tat tat tat att ggt tct gat ggt cag cct aag      577
Gln Ile Asp Gly Lys Tyr Tyr Tyr Ile Gly Ser Asp Gly Gln Pro Lys
                180                 185                 190

aaa aat ttt gct cta acc gtt aat aac aaa gta ctc tac ttc gat aaa      625
Lys Asn Phe Ala Leu Thr Val Asn Asn Lys Val Leu Tyr Phe Asp Lys
            195                 200                 205

aat aca ggt gcc tta acg gac act tct cag tat caa ttt aaa caa ggg      673
Asn Thr Gly Ala Leu Thr Asp Thr Ser Gln Tyr Gln Phe Lys Gln Gly
        210                 215                 220

tta aca aaa tta aac aac gat tat act ccc cac aat caa att gtc aat      721
Leu Thr Lys Leu Asn Asn Asp Tyr Thr Pro His Asn Gln Ile Val Asn
    225                 230                 235

ttt gaa aat acc agt ctt gaa acg att gat aac tat gtc aca gct gat      769
Phe Glu Asn Thr Ser Leu Glu Thr Ile Asp Asn Tyr Val Thr Ala Asp
240                 245                 250                 255
```

-continued

```
tcg tgg tat cgt cct aag gat att tta aag aat ggc aaa acg tgg aca      817
Ser Trp Tyr Arg Pro Lys Asp Ile Leu Lys Asn Gly Lys Thr Trp Thr
                260                 265                 270

gct tca tct gag tct gat ctt cgt ccg ctt tta atg tct tgg tgg cca      865
Ala Ser Ser Glu Ser Asp Leu Arg Pro Leu Leu Met Ser Trp Trp Pro
            275                 280                 285

gat aaa caa acg caa att gct tat ctt aac tac atg aac cag caa gga      913
Asp Lys Gln Thr Gln Ile Ala Tyr Leu Asn Tyr Met Asn Gln Gln Gly
        290                 295                 300

ctt gga act ggt gaa aat tac aca gca gac agc agc caa gaa agt ctc      961
Leu Gly Thr Gly Glu Asn Tyr Thr Ala Asp Ser Ser Gln Glu Ser Leu
    305                 310                 315

aac ctt gct gca caa acc gtt caa gtt aag att gaa act aaa att tct     1009
Asn Leu Ala Ala Gln Thr Val Gln Val Lys Ile Glu Thr Lys Ile Ser
320                 325                 330                 335

caa acg cag caa acc cag tgg ctg cgt gat att atc aat agt ttt gtt     1057
Gln Thr Gln Gln Thr Gln Trp Leu Arg Asp Ile Ile Asn Ser Phe Val
                340                 345                 350

aaa acg caa cca aat tgg aat agt caa aca gaa tcg gat act tca gct     1105
Lys Thr Gln Pro Asn Trp Asn Ser Gln Thr Glu Ser Asp Thr Ser Ala
            355                 360                 365

ggt gaa aaa gat cac ttg caa ggc ggt gct ctg ctt tat agc aac agc     1153
Gly Glu Lys Asp His Leu Gln Gly Gly Ala Leu Leu Tyr Ser Asn Ser
        370                 375                 380

gat aag aca gcc tat gct aat tcc gat tac cgt ctt ttg aac cgc aca     1201
Asp Lys Thr Ala Tyr Ala Asn Ser Asp Tyr Arg Leu Leu Asn Arg Thr
    385                 390                 395

cca acc agt caa acg ggt aaa cca aaa tat ttt gaa gac aat tct tct     1249
Pro Thr Ser Gln Thr Gly Lys Pro Lys Tyr Phe Glu Asp Asn Ser Ser
400                 405                 410                 415

ggt ggc tat gac ttc ctc cta gct aat gat att gat aat tca aat cca     1297
Gly Gly Tyr Asp Phe Leu Leu Ala Asn Asp Ile Asp Asn Ser Asn Pro
                420                 425                 430

gtg gtt caa gct gaa caa tta aac tgg ctt cat tat ctg atg aat tat     1345
Val Val Gln Ala Glu Gln Leu Asn Trp Leu His Tyr Leu Met Asn Tyr
            435                 440                 445

ggt tct att gtc gct aat gat cct gag gct aat ttt gac ggt gtt cgt     1393
Gly Ser Ile Val Ala Asn Asp Pro Glu Ala Asn Phe Asp Gly Val Arg
        450                 455                 460

gtt gat gcc gtt gat aat gtt aat gcc gac ttg ctg cag att gct tcg     1441
Val Asp Ala Val Asp Asn Val Asn Ala Asp Leu Leu Gln Ile Ala Ser
    465                 470                 475

gac tat ttg aaa gcc cat tat ggt gtt gat aag agt gag aaa aat gcg     1489
Asp Tyr Leu Lys Ala His Tyr Gly Val Asp Lys Ser Glu Lys Asn Ala
480                 485                 490                 495

att aat cat ctt tcc att tta gaa gct tgg tca gat aat gat ccc caa     1537
Ile Asn His Leu Ser Ile Leu Glu Ala Trp Ser Asp Asn Asp Pro Gln
                500                 505                 510

tac aat aaa gat act aag ggt gca caa tta ccg att gat aat aaa ctg     1585
Tyr Asn Lys Asp Thr Lys Gly Ala Gln Leu Pro Ile Asp Asn Lys Leu
            515                 520                 525

cgc cta tcg ctt tta tat gct ttg acg cgt cct ctt gaa aaa gat gca     1633
Arg Leu Ser Leu Leu Tyr Ala Leu Thr Arg Pro Leu Glu Lys Asp Ala
        530                 535                 540

agc aat aaa aat gaa att cgc agc gga ctt gag cct gtc ata aca aat     1681
Ser Asn Lys Asn Glu Ile Arg Ser Gly Leu Glu Pro Val Ile Thr Asn
    545                 550                 555

agc ttg aat aac cgt tca gct gaa ggt aaa aat agt gaa cgt atg gct     1729
Ser Leu Asn Asn Arg Ser Ala Glu Gly Lys Asn Ser Glu Arg Met Ala
560                 565                 570                 575
```

-continued

```
aac tat att ttt atc cgc gct cac gac agt gaa gtc caa acg gtt att     1777
Asn Tyr Ile Phe Ile Arg Ala His Asp Ser Glu Val Gln Thr Val Ile
                580                 585                 590

gct aaa att att aaa gct cag att aat ccc aaa aca gat ggt ttg acc     1825
Ala Lys Ile Ile Lys Ala Gln Ile Asn Pro Lys Thr Asp Gly Leu Thr
            595                 600                 605

ttt act ttg gat gaa ttg aag caa gcc ttt aag atc tac aat gaa gac     1873
Phe Thr Leu Asp Glu Leu Lys Gln Ala Phe Lys Ile Tyr Asn Glu Asp
        610                 615                 620

atg cgt cag gct aag aaa aag tac aca caa tcc aat att ccg aca gcc     1921
Met Arg Gln Ala Lys Lys Lys Tyr Thr Gln Ser Asn Ile Pro Thr Ala
    625                 630                 635

tat gct ttg atg ctg tcc aat aaa gat tct att aca cgt ctt tat tat     1969
Tyr Ala Leu Met Leu Ser Asn Lys Asp Ser Ile Thr Arg Leu Tyr Tyr
640                 645                 650                 655

ggt gat atg tac agt gat gac ggt caa tat atg gcg act aaa tcc cct     2017
Gly Asp Met Tyr Ser Asp Asp Gly Gln Tyr Met Ala Thr Lys Ser Pro
                660                 665                 670

tat tat gat gct att gat act tta tta aag gca cgt att aaa tat gcc     2065
Tyr Tyr Asp Ala Ile Asp Thr Leu Leu Lys Ala Arg Ile Lys Tyr Ala
            675                 680                 685

gcc ggt ggt caa gac atg aag atc acc tat gtt gaa ggt gat aaa agt     2113
Ala Gly Gly Gln Asp Met Lys Ile Thr Tyr Val Glu Gly Asp Lys Ser
        690                 695                 700

cat atg gat tgg gat tat aca ggc gtt ttg act tct gtt cgt tat ggt     2161
His Met Asp Trp Asp Tyr Thr Gly Val Leu Thr Ser Val Arg Tyr Gly
    705                 710                 715

aca gga gct aat gaa gct aca gat caa ggc agt gaa gca act aaa aca     2209
Thr Gly Ala Asn Glu Ala Thr Asp Gln Gly Ser Glu Ala Thr Lys Thr
720                 725                 730                 735

caa gga atg gct gtc att acc agc aat aac cct agc ctt aaa ttg aat     2257
Gln Gly Met Ala Val Ile Thr Ser Asn Asn Pro Ser Leu Lys Leu Asn
                740                 745                 750

caa aat gat aaa gta att gtc aat atg ggg gct gcg cat aaa aat caa     2305
Gln Asn Asp Lys Val Ile Val Asn Met Gly Ala Ala His Lys Asn Gln
            755                 760                 765

gag tac cgt ccg ctc ctc tta aca act aaa gat ggt ttg aca agc tac     2353
Glu Tyr Arg Pro Leu Leu Leu Thr Thr Lys Asp Gly Leu Thr Ser Tyr
        770                 775                 780

act tct gat gcc gct gct aaa tcc ctt tat cgc aaa acg aat gat aaa     2401
Thr Ser Asp Ala Ala Ala Lys Ser Leu Tyr Arg Lys Thr Asn Asp Lys
    785                 790                 795

gga gaa tta gtc ttt gat gct agt gac att caa ggt tac ctg aat ccg     2449
Gly Glu Leu Val Phe Asp Ala Ser Asp Ile Gln Gly Tyr Leu Asn Pro
800                 805                 810                 815

caa gta tca ggt tat tta gcc gtt tgg gtt cca gta gga gct agt gat     2497
Gln Val Ser Gly Tyr Leu Ala Val Trp Val Pro Val Gly Ala Ser Asp
                820                 825                 830

aat caa gat gtt cgt gta gca gca agc aat aag gca aat gct act ggt     2545
Asn Gln Asp Val Arg Val Ala Ala Ser Asn Lys Ala Asn Ala Thr Gly
            835                 840                 845

caa gtc tac gaa tca tca agt gct ctt gat tct caa ttg att tac gaa     2593
Gln Val Tyr Glu Ser Ser Ser Ala Leu Asp Ser Gln Leu Ile Tyr Glu
        850                 855                 860

ggt ttc tca aac ttc caa gat ttt gta acg aaa gat tca gac tat act     2641
Gly Phe Ser Asn Phe Gln Asp Phe Val Thr Lys Asp Ser Asp Tyr Thr
    865                 870                 875
```

-continued

```
aat aag aag att gct caa aat gtc caa ctc ttc aaa tct tgg ggt gtc     2689
Asn Lys Lys Ile Ala Gln Asn Val Gln Leu Phe Lys Ser Trp Gly Val
880                 885                 890                 895

act tcc ttt gaa atg gca ccg caa tat gtc tct tct gaa gat ggt tct     2737
Thr Ser Phe Glu Met Ala Pro Gln Tyr Val Ser Ser Glu Asp Gly Ser
                900                 905                 910

ttt cta gac tct att att caa aat ggt tat gcc ttt gag gat cgt tat     2785
Phe Leu Asp Ser Ile Ile Gln Asn Gly Tyr Ala Phe Glu Asp Arg Tyr
            915                 920                 925

gat ctt gct atg agt aag aat aac aaa tac ggt tct cag caa gac atg     2833
Asp Leu Ala Met Ser Lys Asn Asn Lys Tyr Gly Ser Gln Gln Asp Met
        930                 935                 940

att aat gca gtt aaa gct ctg cat aaa agc ggt att cag gtt att gcg     2881
Ile Asn Ala Val Lys Ala Leu His Lys Ser Gly Ile Gln Val Ile Ala
    945                 950                 955

gat tgg gta cca gat caa atc tat aat ctt ccg ggc aaa gaa gtc gta     2929
Asp Trp Val Pro Asp Gln Ile Tyr Asn Leu Pro Gly Lys Glu Val Val
960                 965                 970                 975

acg gct aca cgt gtc aac gat tat ggt gag tat cgc aaa gac tct gaa     2977
Thr Ala Thr Arg Val Asn Asp Tyr Gly Glu Tyr Arg Lys Asp Ser Glu
                980                 985                 990

atc aaa aat aca ctc tat gct gcc aac act aag agt aat ggt aag gat     3025
Ile Lys Asn Thr Leu Tyr Ala Ala Asn Thr Lys Ser Asn Gly Lys Asp
            995                 1000                1005

tat caa gcg aag tat ggc ggt gct ttc ctt agt gaa ctc gct gct aag     3073
Tyr Gln Ala Lys Tyr Gly Gly Ala Phe Leu Ser Glu Leu Ala Ala Lys
        1010                1015                1020

tac cct agt atc ttt aac cgc acg caa att tca aat ggt aag aag att     3121
Tyr Pro Ser Ile Phe Asn Arg Thr Gln Ile Ser Asn Gly Lys Lys Ile
    1025                1030                1035

gat cca agc gaa aaa atc aca gca tgg aaa gca aaa tac ttc aat ggg     3169
Asp Pro Ser Glu Lys Ile Thr Ala Trp Lys Ala Lys Tyr Phe Asn Gly
1040                1045                1050                1055

aca aat att cta ggc cgt ggt gtt ggt tat gtt ctt aaa gat aat gct     3217
Thr Asn Ile Leu Gly Arg Gly Val Gly Tyr Val Leu Lys Asp Asn Ala
                1060                1065                1070

agt gat aaa tac ttt gaa ctg aaa ggg aat caa acc tat ctg cca aaa     3265
Ser Asp Lys Tyr Phe Glu Leu Lys Gly Asn Gln Thr Tyr Leu Pro Lys
            1075                1080                1085

cag atg act aac aaa gaa gct tcg act ggt ttt gtt aat gat ggc aat     3313
Gln Met Thr Asn Lys Glu Ala Ser Thr Gly Phe Val Asn Asp Gly Asn
        1090                1095                1100

ggg atg act ttc tat tca act agt ggt tat caa gcc aag aac agc ttt     3361
Gly Met Thr Phe Tyr Ser Thr Ser Gly Tyr Gln Ala Lys Asn Ser Phe
    1105                1110                1115

gtt caa gat gcc aaa gga aac tgg tat tac ttt gat aat aat ggc cat     3409
Val Gln Asp Ala Lys Gly Asn Trp Tyr Tyr Phe Asp Asn Asn Gly His
1120                1125                1130                1135

atg gtt tat ggc tta cag cag cta aat ggc gaa gtg caa tac ttt tta     3457
Met Val Tyr Gly Leu Gln Gln Leu Asn Gly Glu Val Gln Tyr Phe Leu
                1140                1145                1150

tca aat ggt gtt caa ttg cgt gaa tct ttc ttg gaa aac gct gat ggc     3505
Ser Asn Gly Val Gln Leu Arg Glu Ser Phe Leu Glu Asn Ala Asp Gly
            1155                1160                1165

agc aag aac tat ttt ggt cat cta gga aat aga tat agt aat ggt tat     3553
Ser Lys Asn Tyr Phe Gly His Leu Gly Asn Arg Tyr Ser Asn Gly Tyr
        1170                1175                1180

tat tca ttt gat aat gat agt aag tgg cgt tat ttt gat gcc agt gga     3601
Tyr Ser Phe Asp Asn Asp Ser Lys Trp Arg Tyr Phe Asp Ala Ser Gly
    1185                1190                1195
```

-continued gtc atg gct gta ggt ttg aaa aca att aac ggc aat acg cag tac ttt 3649
Val Met Ala Val Gly Leu Lys Thr Ile Asn Gly Asn Thr Gln Tyr Phe
1200 1205 1210 1215 gat caa gat ggt tat caa gtc aaa ggt gct tgg ata aca ggc agc gat 3697
Asp Gln Asp Gly Tyr Gln Val Lys Gly Ala Trp Ile Thr Gly Ser Asp
1220 1225 1230 ggc aaa aag cgt tat ttt gat gac gga tct gga aat atg gct gtt aat 3745
Gly Lys Lys Arg Tyr Phe Asp Asp Gly Ser Gly Asn Met Ala Val Asn
1235 1240 1245 cgt ttt gca aat gat aaa aac ggc gat tgg tac tat ctc aat tca gat 3793
Arg Phe Ala Asn Asp Lys Asn Gly Asp Trp Tyr Tyr Leu Asn Ser Asp
1250 1255 1260 ggc att gcc ttg gtt ggt gtc caa acc att aat ggt aag act tat tac 3841
Gly Ile Ala Leu Val Gly Val Gln Thr Ile Asn Gly Lys Thr Tyr Tyr
1265 1270 1275 ttt ggc caa gat ggt aag caa atc aaa ggt aaa att att aca gac aat 3889
Phe Gly Gln Asp Gly Lys Gln Ile Lys Gly Lys Ile Ile Thr Asp Asn
1280 1285 1290 1295 ggt aag ctg aaa tat ttc ctt gcc aat tca gga gaa tta gca cgc aat 3937
Gly Lys Leu Lys Tyr Phe Leu Ala Asn Ser Gly Glu Leu Ala Arg Asn
1300 1305 1310 atc ttt gca aca gac agt caa aac aat tgg tat tac ttt ggt tca gac 3985
Ile Phe Ala Thr Asp Ser Gln Asn Asn Trp Tyr Tyr Phe Gly Ser Asp
1315 1320 1325 ggt gtt gcg gtt aca ggc agt cag aca att gct ggt aaa aag ctc tat 4033
Gly Val Ala Val Thr Gly Ser Gln Thr Ile Ala Gly Lys Lys Leu Tyr
1330 1335 1340 ttt gca agc gac gga aaa caa gtc aaa ggc agc ttt gtc act tat aat 4081
Phe Ala Ser Asp Gly Lys Gln Val Lys Gly Ser Phe Val Thr Tyr Asn
1345 1350 1355 ggt aaa gtt cat tat tat cat gct gac tca gga gaa tta caa gtt aac 4129
Gly Lys Val His Tyr Tyr His Ala Asp Ser Gly Glu Leu Gln Val Asn
1360 1365 1370 1375 cgc ttt gaa gca gat aag gat ggt aat tgg tat tat ctt gat tca aat 4177
Arg Phe Glu Ala Asp Lys Asp Gly Asn Trp Tyr Tyr Leu Asp Ser Asn
1380 1385 1390 ggt gaa gct ctg aca ggt agc caa cgc att aac gat cag cgt gtc ttc 4225
Gly Glu Ala Leu Thr Gly Ser Gln Arg Ile Asn Asp Gln Arg Val Phe
1395 1400 1405 ttt acg cga gaa gga aaa caa gtt aaa ggt gat gtt gct tat gat gag 4273
Phe Thr Arg Glu Gly Lys Gln Val Lys Gly Asp Val Ala Tyr Asp Glu
1410 1415 1420 cga agg ctt ctc gta tat aga t aagatagtgg taaca 4310
Arg Arg Leu Leu Val Tyr Arg
1425 1430

<210> SEQ ID NO 2
<211> LENGTH: 1430
<212> TYPE: PRT
<213> ORGANISM: Streptococcus mutans

<400> SEQUENCE: 2

Met Glu Thr Lys Arg Arg Tyr Lys Met His Lys Val Lys Lys His Trp
1 5 10 15

Val Thr Val Ala Val Ala Ser Gly Leu Ile Thr Leu Gly Thr Thr Thr
20 25 30

Leu Gly Ser Ser Val Ser Ala Glu Thr Glu Gln Gln Thr Ser Asp Lys
35 40 45

-continued

Val Val Thr Gln Lys Ser Glu Asp Asp Lys Ala Ala Ser Glu Ser Ser
50 55 60

Gln Thr Asp Ala Pro Lys Thr Lys Gln Ala Gln Thr Glu Gln Thr Gln
65 70 75 80

Ala Gln Ser Gln Ala Asn Val Ala Asp Thr Ser Thr Ser Ile Thr Lys
85 90 95

Glu Thr Pro Ser Gln Asn Ile Thr Thr Gln Ala Asn Ser Asp Asp Lys
100 105 110

Thr Val Thr Asn Thr Lys Ser Glu Glu Ala Gln Thr Ser Glu Glu Arg
115 120 125

Thr Lys Gln Ser Glu Glu Ala Gln Thr Thr Ala Ser Ser Gln Ala Leu
130 135 140

Thr Gln Ala Lys Ala Glu Leu Thr Lys Gln Arg Gln Thr Ala Ala Gln
145 150 155 160

Glu Asn Lys Asn Pro Val Asp Leu Ala Ala Ile Pro Asn Val Lys Gln
165 170 175

Ile Asp Gly Lys Tyr Tyr Tyr Ile Gly Ser Asp Gly Gln Pro Lys Lys
180 185 190

Asn Phe Ala Leu Thr Val Asn Asn Lys Val Leu Tyr Phe Asp Lys Asn
195 200 205

Thr Gly Ala Leu Thr Asp Thr Ser Gln Tyr Gln Phe Lys Gln Gly Leu
210 215 220

Thr Lys Leu Asn Asn Asp Tyr Thr Pro His Asn Gln Ile Val Asn Phe
225 230 235 240

Glu Asn Thr Ser Leu Glu Thr Ile Asp Asn Tyr Val Thr Ala Asp Ser
245 250 255

Trp Tyr Arg Pro Lys Asp Ile Leu Lys Asn Gly Lys Thr Trp Thr Ala
260 265 270

Ser Ser Glu Ser Asp Leu Arg Pro Leu Leu Met Ser Trp Trp Pro Asp
275 280 285

Lys Gln Thr Gln Ile Ala Tyr Leu Asn Tyr Met Asn Gln Gln Gly Leu
290 295 300

Gly Thr Gly Glu Asn Tyr Thr Ala Asp Ser Ser Gln Glu Ser Leu Asn
305 310 315 320

Leu Ala Ala Gln Thr Val Gln Val Lys Ile Glu Thr Lys Ile Ser Gln
325 330 335

Thr Gln Gln Thr Gln Trp Leu Arg Asp Ile Ile Asn Ser Phe Val Lys
340 345 350

Thr Gln Pro Asn Trp Asn Ser Gln Thr Glu Ser Asp Thr Ser Ala Gly
355 360 365

Glu Lys Asp His Leu Gln Gly Gly Ala Leu Leu Tyr Ser Asn Ser Asp
370 375 380

Lys Thr Ala Tyr Ala Asn Ser Asp Tyr Arg Leu Leu Asn Arg Thr Pro
385 390 395 400

Thr Ser Gln Thr Gly Lys Pro Lys Tyr Phe Glu Asp Asn Ser Ser Gly
405 410 415

Gly Tyr Asp Phe Leu Leu Ala Asn Asp Ile Asp Asn Ser Asn Pro Val
420 425 430

Val Gln Ala Glu Gln Leu Asn Trp Leu His Tyr Leu Met Asn Tyr Gly
435 440 445

Ser Ile Val Ala Asn Asp Pro Glu Ala Asn Phe Asp Gly Val Arg Val
450 455 460

-continued

Asp Ala Val Asp Asn Val Asn Ala Asp Leu Leu Gln Ile Ala Ser Asp
465 470 475 480

Tyr Leu Lys Ala His Tyr Gly Val Asp Lys Ser Glu Lys Asn Ala Ile
485 490 495

Asn His Leu Ser Ile Leu Glu Ala Trp Ser Asp Asn Asp Pro Gln Tyr
500 505 510

Asn Lys Asp Thr Lys Gly Ala Gln Leu Pro Ile Asp Asn Lys Leu Arg
515 520 525

Leu Ser Leu Leu Tyr Ala Leu Thr Arg Pro Leu Glu Lys Asp Ala Ser
530 535 540

Asn Lys Asn Glu Ile Arg Ser Gly Leu Glu Pro Val Ile Thr Asn Ser
545 550 555 560

Leu Asn Asn Arg Ser Ala Glu Gly Lys Asn Ser Glu Arg Met Ala Asn
565 570 575

Tyr Ile Phe Ile Arg Ala His Asp Ser Glu Val Gln Thr Val Ile Ala
580 585 590

Lys Ile Ile Lys Ala Gln Ile Asn Pro Lys Thr Asp Gly Leu Thr Phe
595 600 605

Thr Leu Asp Glu Leu Lys Gln Ala Phe Lys Ile Tyr Asn Glu Asp Met
610 615 620

Arg Gln Ala Lys Lys Lys Tyr Thr Gln Ser Asn Ile Pro Thr Ala Tyr
625 630 635 640

Ala Leu Met Leu Ser Asn Lys Asp Ser Ile Thr Arg Leu Tyr Tyr Gly
645 650 655

Asp Met Tyr Ser Asp Asp Gly Gln Tyr Met Ala Thr Lys Ser Pro Tyr
660 665 670

Tyr Asp Ala Ile Asp Thr Leu Leu Lys Ala Arg Ile Lys Tyr Ala Ala
675 680 685

Gly Gly Gln Asp Met Lys Ile Thr Tyr Val Glu Gly Asp Lys Ser His
690 695 700

Met Asp Trp Asp Tyr Thr Gly Val Leu Thr Ser Val Arg Tyr Gly Thr
705 710 715 720

Gly Ala Asn Glu Ala Thr Asp Gln Gly Ser Glu Ala Thr Lys Thr Gln
725 730 735

Gly Met Ala Val Ile Thr Ser Asn Asn Pro Ser Leu Lys Leu Asn Gln
740 745 750

Asn Asp Lys Val Ile Val Asn Met Gly Ala Ala His Lys Asn Gln Glu
755 760 765

Tyr Arg Pro Leu Leu Leu Thr Thr Lys Asp Gly Leu Thr Ser Tyr Thr
770 775 780

Ser Asp Ala Ala Ala Lys Ser Leu Tyr Arg Lys Thr Asn Asp Lys Gly
785 790 795 800

Glu Leu Val Phe Asp Ala Ser Asp Ile Gln Gly Tyr Leu Asn Pro Gln
805 810 815

Val Ser Gly Tyr Leu Ala Val Trp Val Pro Val Gly Ala Ser Asp Asn
820 825 830

Gln Asp Val Arg Val Ala Ala Ser Asn Lys Ala Asn Ala Thr Gly Gln
835 840 845

Val Tyr Glu Ser Ser Ser Ala Leu Asp Ser Gln Leu Ile Tyr Glu Gly
850 855 860

Phe Ser Asn Phe Gln Asp Phe Val Thr Lys Asp Ser Asp Tyr Thr Asn
865 870 875 880

-continued

```
Lys Lys Ile Ala Gln Asn Val Gln Leu Phe Lys Ser Trp Gly Val Thr
            885                 890                 895

Ser Phe Glu Met Ala Pro Gln Tyr Val Ser Ser Glu Asp Gly Ser Phe
            900                 905                 910

Leu Asp Ser Ile Ile Gln Asn Gly Tyr Ala Phe Glu Asp Arg Tyr Asp
        915                 920                 925

Leu Ala Met Ser Lys Asn Asn Lys Tyr Gly Ser Gln Gln Asp Met Ile
    930                 935                 940

Asn Ala Val Lys Ala Leu His Lys Ser Gly Ile Gln Val Ile Ala Asp
945                 950                 955                 960

Trp Val Pro Asp Gln Ile Tyr Asn Leu Pro Gly Lys Glu Val Val Thr
            965                 970                 975

Ala Thr Arg Val Asn Asp Tyr Gly Glu Tyr Arg Lys Asp Ser Glu Ile
            980                 985                 990

Lys Asn Thr Leu Tyr Ala Ala Asn Thr Lys Ser Asn Gly Lys Asp Tyr
        995                 1000                1005

Gln Ala Lys Tyr Gly Gly Ala Phe Leu Ser Glu Leu Ala Ala Lys Tyr
    1010                1015                1020

Pro Ser Ile Phe Asn Arg Thr Gln Ile Ser Asn Gly Lys Lys Ile Asp
1025                1030                1035                1040

Pro Ser Glu Lys Ile Thr Ala Trp Lys Ala Lys Tyr Phe Asn Gly Thr
            1045                1050                1055

Asn Ile Leu Gly Arg Gly Val Gly Tyr Val Leu Lys Asp Asn Ala Ser
            1060                1065                1070

Asp Lys Tyr Phe Glu Leu Lys Gly Asn Gln Thr Tyr Leu Pro Lys Gln
        1075                1080                1085

Met Thr Asn Lys Glu Ala Ser Thr Gly Phe Val Asn Asp Gly Asn Gly
    1090                1095                1100

Met Thr Phe Tyr Ser Thr Ser Gly Tyr Gln Ala Lys Asn Ser Phe Val
1105                1110                1115                1120

Gln Asp Ala Lys Gly Asn Trp Tyr Tyr Phe Asp Asn Asn Gly His Met
            1125                1130                1135

Val Tyr Gly Leu Gln Gln Leu Asn Gly Glu Val Gln Tyr Phe Leu Ser
            1140                1145                1150

Asn Gly Val Gln Leu Arg Glu Ser Phe Leu Glu Asn Ala Asp Gly Ser
        1155                1160                1165

Lys Asn Tyr Phe Gly His Leu Gly Asn Arg Tyr Ser Asn Gly Tyr Tyr
    1170                1175                1180

Ser Phe Asp Asn Asp Ser Lys Trp Arg Tyr Phe Asp Ala Ser Gly Val
1185                1190                1195                1200

Met Ala Val Gly Leu Lys Thr Ile Asn Gly Asn Thr Gln Tyr Phe Asp
            1205                1210                1215

Gln Asp Gly Tyr Gln Val Lys Gly Ala Trp Ile Thr Gly Ser Asp Gly
            1220                1225                1230

Lys Lys Arg Tyr Phe Asp Asp Gly Ser Gly Asn Met Ala Val Asn Arg
        1235                1240                1245

Phe Ala Asn Asp Lys Asn Gly Asp Trp Tyr Tyr Leu Asn Ser Asp Gly
    1250                1255                1260

Ile Ala Leu Val Gly Val Gln Thr Ile Asn Gly Lys Thr Tyr Tyr Phe
1265                1270                1275                1280

Gly Gln Asp Gly Lys Gln Ile Lys Gly Lys Ile Ile Thr Asp Asn Gly
            1285                1290                1295
```

-continued

```
Lys Leu Lys Tyr Phe Leu Ala Asn Ser Gly Glu Leu Ala Arg Asn Ile
            1300                1305                1310

Phe Ala Thr Asp Ser Gln Asn Asn Trp Tyr Tyr Phe Gly Ser Asp Gly
        1315                1320                1325

Val Ala Val Thr Gly Ser Gln Thr Ile Ala Gly Lys Lys Leu Tyr Phe
    1330                1335                1340

Ala Ser Asp Gly Lys Gln Val Lys Gly Ser Phe Val Thr Tyr Asn Gly
1345                1350                1355                1360

Lys Val His Tyr Tyr His Ala Asp Ser Gly Glu Leu Gln Val Asn Arg
                1365                1370                1375

Phe Glu Ala Asp Lys Asp Gly Asn Trp Tyr Tyr Leu Asp Ser Asn Gly
            1380                1385                1390

Glu Ala Leu Thr Gly Ser Gln Arg Ile Asn Asp Gln Arg Val Phe Phe
        1395                1400                1405

Thr Arg Glu Gly Lys Gln Val Lys Gly Asp Val Ala Tyr Asp Glu Arg
    1410                1415                1420

Arg Leu Leu Val Tyr Arg
1425                1430
```